United States Patent
Boute et al.

(10) Patent No.: US 9,538,919 B2
(45) Date of Patent: Jan. 10, 2017

(54) SYSTEM AND METHOD FOR IMPROVED ISCHEMIA AND ACUTE MYOCARDIAL INFARCTION DETECTION

(75) Inventors: Willem Boute, Brummen (NL); David Robert Hampton, Woodinville, WA (US); Wilbert Wesselink, Doesburg (NL); Anna Pietersma, Doesburg (NL)

(73) Assignee: Medtronic, Inc., Minneapolis, MN (US)

( * ) Notice: Subject to any disclaimer, the term of this patent is extended or adjusted under 35 U.S.C. 154(b) by 2520 days.

(21) Appl. No.: 12/170,037

(22) Filed: Jul. 9, 2008

(65) Prior Publication Data

US 2010/0010361 A1  Jan. 14, 2010

(51) Int. Cl.
A61B 5/04 (2006.01)
A61B 5/00 (2006.01)
A61B 5/0452 (2006.01)
A61B 5/053 (2006.01)
A61N 1/362 (2006.01)
A61N 1/368 (2006.01)

(52) U.S. Cl.
CPC ........... *A61B 5/0031* (2013.01); *A61B 5/0452* (2013.01); *A61B 5/053* (2013.01); *A61B 5/4035* (2013.01); *A61N 1/368* (2013.01); *A61N 1/3627* (2013.01)

(58) Field of Classification Search
CPC .... A61B 5/0452; A61B 5/04012; A61B 5/053
USPC ........................................................ 600/515
See application file for complete search history.

(56) References Cited

U.S. PATENT DOCUMENTS

| | | | |
|---|---|---|---|
| 5,323,783 A * | 6/1994 | Henkin et al. | 600/516 |
| 6,361,503 B1 * | 3/2002 | Starobin et al. | 600/508 |
| 6,368,284 B1 | 4/2002 | Bardy | |
| 6,609,023 B1 * | 8/2003 | Fischell et al. | 600/515 |
| 7,181,269 B1 * | 2/2007 | Kroll | 600/517 |
| 2004/0039265 A1 | 2/2004 | Bardy | |
| 2005/0256417 A1 | 11/2005 | Fischell et al. | |

OTHER PUBLICATIONS

Bailon, R. et al., "Robust Measure of ST/HR Hysteresis in Stress Test ECG Recordings," IEEE, Computers in Cardiology, vol. 29, 2002, pp. 329-332.

(Continued)

*Primary Examiner* — Amanda Patton
*Assistant Examiner* — Philip C Edwards (57) ABSTRACT

A system and method are provided for the detection of a heart-related condition by obtaining information in real-time when a condition is initially identified as potentially occurring. A physical exercise and recovery episode is initially detected from physiological signals sensed in a patient. Once detected, a HR-ST segment deviation hysteresis analysis is performed in an implantable medical device (IMD) from certain physiological signals over portions of the exercise and recovery episode to identify the probability that a certain condition is occurring. Once a desired level of probability that the heart-related condition has been detected exists, data utilized in the analysis can be transmitted remotely for clinical review and confirmation of the device's detection of the condition. The patient may be prompted to answer questions related to symptoms that patient is experiencing through an input device in order further confirm the probability that the condition is occurring in the patient.

25 Claims, 6 Drawing Sheets (56) References Cited

OTHER PUBLICATIONS

Lehtinen, "Diagnostic and Prognostic Value of ST/HR Hysteresis", Journal of the International Society for Bioelectromagnetism, 2000, vol. 2, No. 1, 3 pages.
Viik et al., "The Effect of Lead Selection on Traditional And Heart Rate-Adjusted ST Segment Analysis in the Detection of Coronary Artery Disease During Exercise Testing", The American Heart Journal, Sep. 1997, vol. 134, No. 3, pp. 488-494.
Improved Detection of Coronary Artery Disease by Novel Methods of Exercise ECG Analysis—A Multicenter Study, located at http://www.bem.fi/bem/research/sthr/sthr.htm, last updated Mar. 10, 1998, 9 pages.

\* cited by examiner

SYSTEM AND METHOD FOR IMPROVED ISCHEMIA AND ACUTE MYOCARDIAL INFARCTION DETECTION

TECHNICAL FIELD

This disclosure relates generally to medical devices and more particularly to a system and method for detecting cardiac ischemia, changes in the patient risk for ischemic events, and the onset of acute myocardial infarction.

BACKGROUND

Historically, acute myocardial infarction (AMI) events have been diagnosed in a patient when at least two of the following three criteria are satisfied: (1) ischemic chest pain typically associated with AMI, (2) electrocardiogram (ECG) findings typically associated with AMI (e.g., abrupt and sustained ST segment deviation and later appearance of pathological Q-waves), and (3) raised concentrations of troponin or creatine kinase (CK) in serum. Angina is diagnosed as pain or chest discomfort of cardiac source, elicited by exertion or emotional stress and relieved by nitrates: dangerous unstable angina (UA) is associated with new, progressive, or crescendo severity of symptoms. In both acute myocardial infarction (AMI) and unstable angina (UA), it is important to document to pattern of changes associated with symptoms and exertion, and to stratify risk by assessing the ECG abnormalities occurring during exercise.

It has been difficult for prior medical devices, either implantable or external, to detect and assess these conditions with satisfactory levels of sensitivity and specificity using the above criteria. For example, in AMI, troponin levels are difficult to access through an insertable loop recorder, while angina assessment has not been performed in association with activity parameters. These difficulties in detection have led to the late recognition of increased ischemic risk, or of ischemia, angina, or AMI events by a patient in seeking assistance. In all cases, this leads to long delays in recognition by the patient, further delaying actions by medical personnel, including measures to reduce risk and to deliver therapies to the patient, such as fibrinolysis or percutaneous coronary intervention (PCI).

SUMMARY

A system and method are provided for the detection of ischemia, unstable angina (UA), acute myocardial infarction (AMI) or other heart-related diseases and conditions using markers having superior discriminative capacity compared to conventional markers. In one or more embodiments, the method includes initially detecting a physical exercise and recovery episode in a patient, where such exercise detection may include detecting the occurrence and intensity of actual physical exercise by the patient or may further include detecting other non-physical exercise circumstances in which heart rate and activity levels of the patient are elevated, or stress situations where heart-rate is elevated in the absence of physical activity, and/or associated with changes in autonomic tone (as indicated by changes in, for example, R-R variability or conduction times (e.g. QT interval)). Once detected, the method performs a heart rate (HR)-ST segment deviation hysteresis analysis (e.g., ST segment depression or elevation) over the course of the physical exercise and recovery episode to identify the probability that ischemia, unstable angina (UA), acute myocardial infarction (AMI) or another heart-related condition is occurring in a patient. In one or more embodiments, the HR-ST segment hysteresis analysis includes measuring HR and ST segment changes from a received electrocardiogram (ECG) signal and then analyzing measured information to determining: (i) a detailed analysis of an initial recovery period after exercise, (ii) the prevailing direction of the HR-ST hysteresis during the exercise and recovery episode, and (iii) the average magnitude of the HR-ST hysteresis during the exercise and recovery episode. From this analysis, a probability that ischemia, unstable angina (UA), acute myocardial infarction (AMI) or another heart-related disease is occurring in the patient is determined.

In one or more embodiments, once a desired level of probability exists that the particular heart-related disease has been detected, the data utilized in the HR-ST segment hysteresis analysis as well as previously collected data or other data related to other sensed physiological conditions can be transmitted to a physician, clinician or call center for review. The actual data can then be compared against historical or baseline data to further to provide an added level of certainty to the detection of the heart-related disease.

In one or more embodiments, once a desired level of probability exists that the particular heart-related disease has been detected, the method may further prompt the patient, a physician or another individual to answer at least one question related to particular symptoms that patient is experiencing that are related to the potentially detected heart-related disease. Such responses to the symptom-related questions may further be transmitted together with actual measured data or separately to the physician, clinician or call center for use in further providing yet another added level of certainty to the detection of the heart-related disease.

In one or more embodiments, once the probability that the particular heart-related disease is being experienced by the patient meets a certain threshold, the method may further provide instructions to the patient, a physician or a clinician to take certain actions for treating the diagnosed disease, provide instructions for collecting additional physiological condition data, and/or cause certain therapies to be delivered to the patient.

The system for detecting ischemia, unstable angina (UA), acute myocardial infarction (AMI) or other heart-related diseases may be implemented in an implantable or external medical device or a combination thereof. The system includes one or more physiological sensors coupled to a signal processing controller for deriving multiple physiological parameters to identify a physical exercise and recovery episode in a patient. Upon detection of the exercise and recovery episode, the physiological sensors further provide electrocardiogram (ECG) signal information to the a signal processing controller for performing the HR-ST segment deviation hysteresis analysis over the course of the physical exercise and recovery episode. The system further includes processing circuitry for computing the probability that a particular heart-related disease has been detected from the HR-ST segment hysteresis analysis, for transferring the collected data utilized in the HR-ST segment hysteresis analysis as well as previously collected data or other data related to other sensed physiological conditions to a physician, clinician or call center for review, and for prompting an external patient-accessible device to query the patient or another individual with questions related to particular symptoms that the patient is experiencing that are related to the potentially detected heart-related disease.

In some embodiments, when the probability that the particular heart-related disease is being experienced by the patient meets a certain threshold, the system may include components for providing instructions to the patient, a physician or a clinician to take certain actions for treating the diagnosed disease, providing instructions for collecting additional physiological condition data, and/or causing certain therapies to be delivered to the patient.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The invention provides a method and apparatus for detecting ischemia, unstable angina (UA), acute myocardial infarction (AMI: STEMI and NSTEMI) and/or other heart-related conditions and providing a response thereto. The invention may be implemented in implantable medical devices (IMDs) that include sensing capabilities for monitoring physiological conditions and may include alert and therapy delivery capabilities. An IMD in which the invention is implemented may be primarily intended for detecting heart-related conditions (e.g., ischemia or acute myocardial infarction) or may primarily be intended for other purposes. For example, the IMD may comprise any type of implanted device including, but not limited to cardiac pacemakers, implantable cardioverter-defibrillators (ICDs), implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patent. Telemetry is used to communicate sensed information from the IMD to an external medical device so that analysis of the sensed information can be performed. Telemetry is further used to communicate information or instructions from external medical devices to the IMD.

The invention may also be implemented in external medical devices that may be used for monitoring of a patient for detecting ischemia, UA, AMI, and/or other heart diseases at a variety of locations, such as a patient's home, a physician's office, a hospital or a treating emergency technician. In the description that follows, various embodiments of the invention are described relating to the detection of these conditions. The methods and system provided by the present invention, however, are not limited to the detection of ischemia, UA, and AMI but may be extended to the detection of other types of heart conditions or other physiological diseases and conditions by monitoring respective physiological conditions.

Figure 1:
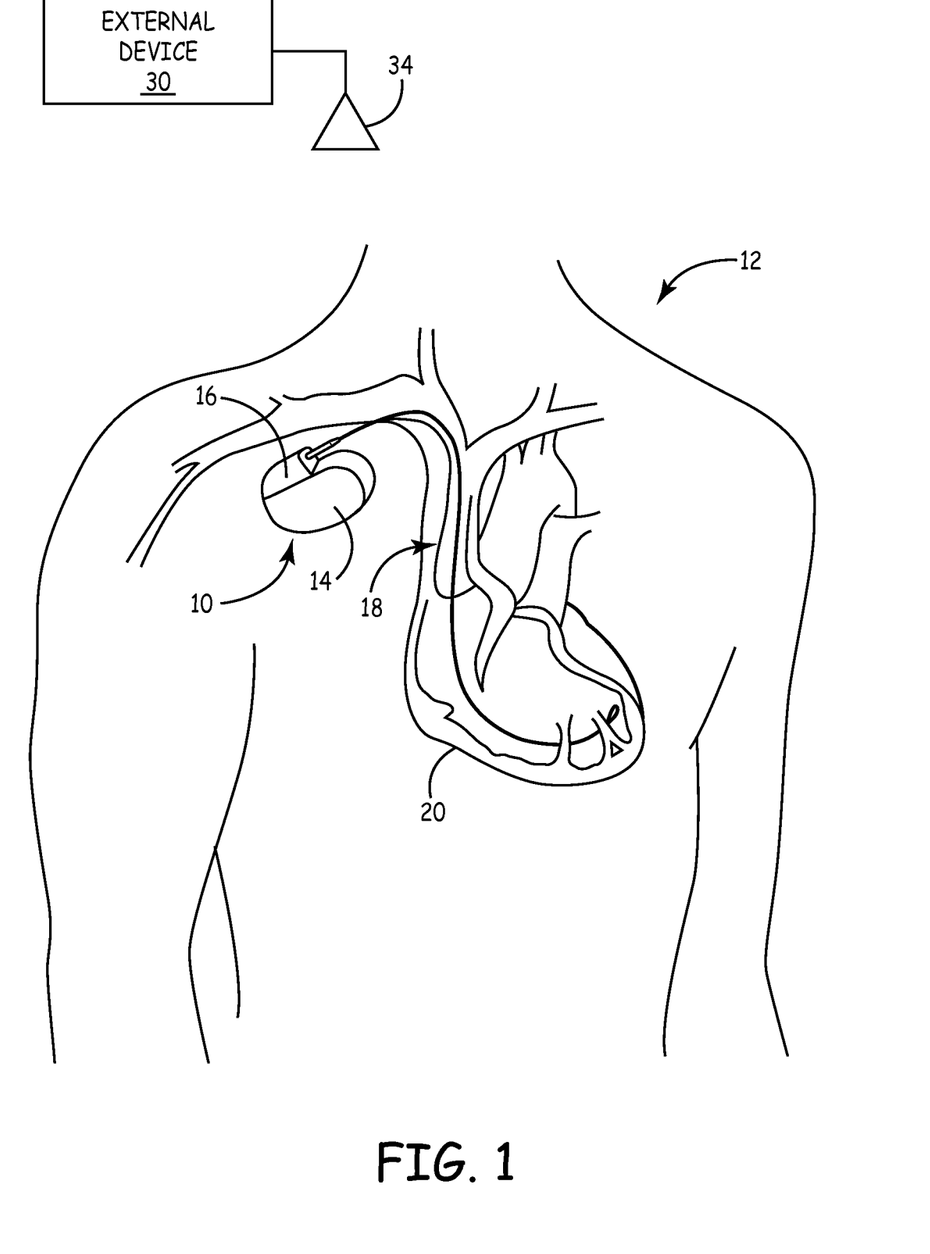
FIG. 1 illustrates an implantable medical device in accordance with an embodiment of the present disclosure implanted in a human body.

FIG. 1 is a simplified schematic view of one type of implantable medical device ("IMD") 10 implanted within a human body 12 in which one or more embodiments of the invention may be implemented. IMD 10 comprises a hermetically sealed enclosure 14 and connector module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 1, it is understood that IMD 10 may comprise any type of implanted device. IMD 10 collects and processes data from one or more sensors for deriving parameters used in computing a probability that an AMI is occurring in the patient in which IMD 10 is implanted.

Figure 2:
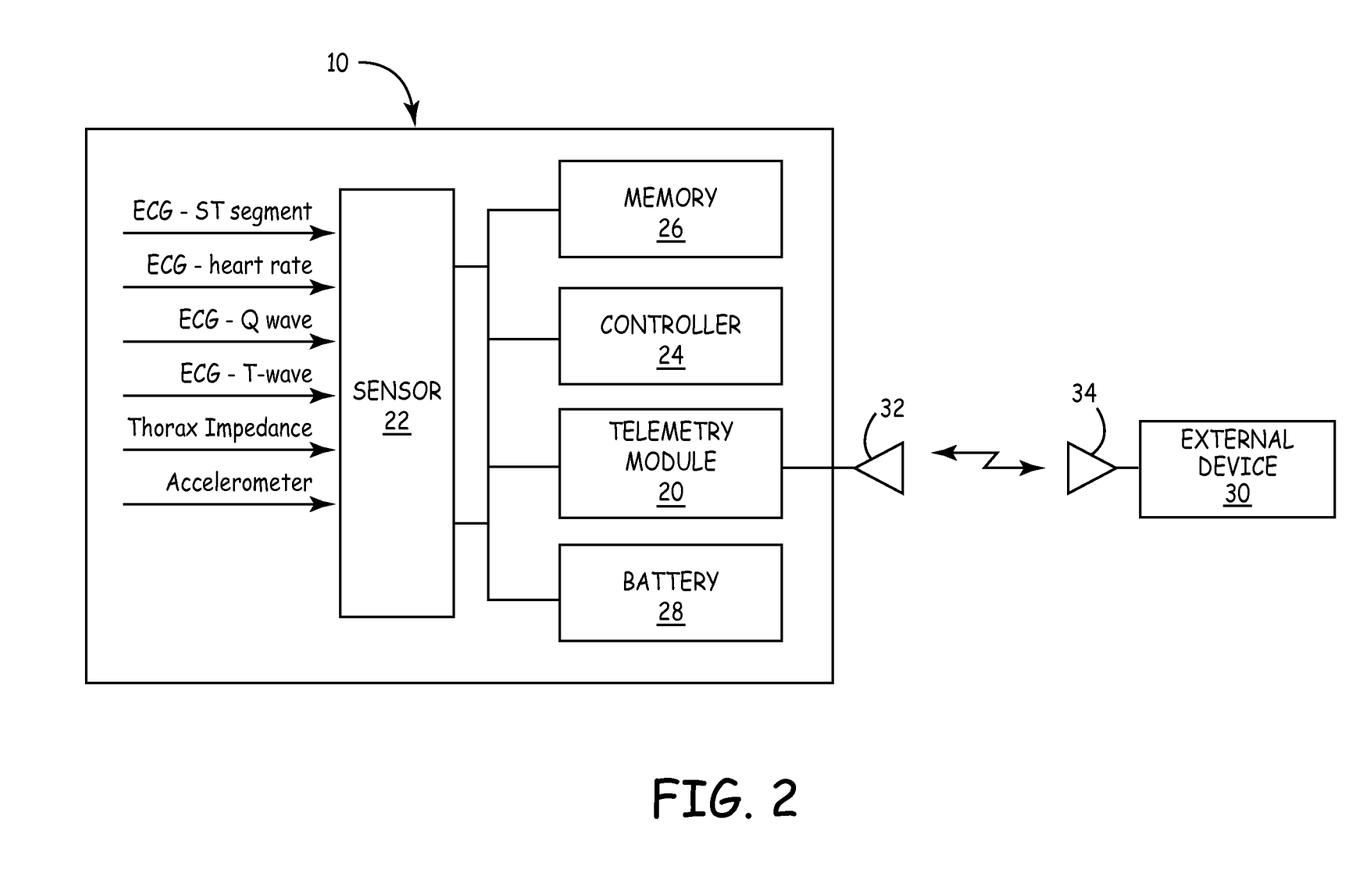
FIG. 2 is a block diagram illustrating the various components of one embodiment of an implantable medical device configured to operate in accordance with the present disclosure.

FIG. 2 is a block diagram illustrating the constituent components of IMD 10 in accordance with one or more embodiments having a microprocessor-based architecture. IMD 10 is shown as including telemetry module 20, at least one sensor 22 for sensing physiological signals, processor or controller 24, memory 26, battery 28 and other components as appropriate to produce the desired functionalities of the device.

Controller 24 may be implemented with any type of microprocessor, digital signal processor, application specific integrated circuit (ASIC), field programmable gate array (FPGA) or other integrated or discrete logic circuitry programmed or otherwise configured to provide functionality as described herein. Controller 24 executes instructions stored in memory 26 to provide functionality as described herein. Instructions provided to controller 24 may be executed in any manner, using any data structures, architecture, programming language and/or other techniques. Memory 26 is any storage medium capable of maintaining digital data and instructions provided to controller 24 such as a static or dynamic random access memory (RAM), read-only memory (ROM), non-volatile random access memory (NVRAM), electrically erasable programmable read-only memory (EE- PROM), flash memory, or any other electronic, magnetic, optical or other storage medium.

As further shown in FIG. 1, IMD 10 may receive one or more cardiac leads 18 for connection to circuitry enclosed within the housing 14. In one or more embodiments, IMD 10 collects electrocardiogram (ECG) signals for use in deriving one or more heart rate related parameters, such as ST segment evaluation, Q-wave analysis (e.g., duration and amplitude), T-wave analysis (e.g., trend analysis, inversion), heart rate or other parameters for use in detecting heart-related conditions, as known to those skilled in the art. Other auxiliary leads may further be connected to both IMD 10 and the patient's body for detecting other physiological conditions, such as thorax impedance signals used for respiratory analysis (e.g., respiratory rate, breathing depth, minute ventilation, etc.), accelerometer signals for sensing patient physical activity and positioning, as well as other types of physiological signals that can utilized as known in the art to detect heart-related conditions. The use of thorax impedance signals for respiratory analysis is known in the art, for example in rate responsive cardiac pacemakers.

Cardiac leads 18 may include, for example, pacing electrodes and defibrillation coil electrodes (not shown) in the event IMD 10 is configured to provide pacing, cardioversion and/or defibrillation. In addition, cardiac leads 18 may deliver pacing stimuli in a coordinated fashion to provide pacing pulses, cardiac resynchronization extra systolic stimulation therapy or other benefits.

In operation, IMD 10 obtains data from physiological signals via electrodes and/or sensors 22 deployed on leads 18 and/or other sources. This data is provided to controller 24, which suitably analyzes the data, stores appropriate data in memory 26, and/or provides a response or report as appropriate. Any parameters indicating a likelihood of the occurrence of ischemia, UA, AMI or other heart-related conditions can lead to further investigation by IMD 10 or lead IMD 10 to provide notification of its detection of the condition that can be responded to by intervention of a physician or in an automated manner. In various embodiments, IMD 10 prompts a patient to respond to specific questions that further assist in the detection of the heart-related condition and may activate an alert upon determination of the condition with sufficient specificity. Alternatively or in addition to alert activation. IMD 10 may select or adjust a therapy and coordinate the delivery of the therapy by IMD 10 or another appropriate device, which could be another IMD or an external device adapted to communicate with IMD 10 and respond to instructions received from IMD 10 or an external device.

Communication between IMD 10 and another device can occur via telemetry, such as a long-distance telemetry system through the telemetry module 20. Telemetry module 20 may comprise any unit capable of facilitating wireless data transfer between IMD 10 and an external device 30, where external device 30 may comprise an external medical device, a programming device, a remote telemetry station, a physician-activated device, a patient-activated device, a mobile handheld unit (e.g., mobile phone, PDA, etc.), a personal computer, an in-home monitoring device, a patient-wearable device, a display device or any other type of device capable of sending and receiving signals to and from IMD 10. Telemetry module 20 and external device 30 are respectively coupled to antennas 32 and 34 for facilitating the wireless data transfer. Telemetry module 20 may be configured to perform any type of wireless communication. For example, telemetry module 20 may send and receive radio frequency (RF) signals, infrared (IR) frequency signals, or other electromagnetic signals. In the case of electromagnetic signals, antennas 32 and 34 may comprise coils for transmitting and receiving signals when positioned adjacent to one another. Any of a variety of modulation techniques may be used to modulate data on a respective electromagnetic carrier wave. Alternatively, telemetry module 20 may use sound waves for communicating data, or may use the patient's tissue as the transmission medium for communicating with a programmer positioned on the patients skin. In any event, telemetry module 20 facilitates wireless data transfer between IMD 10 and external device 30. Other types of wired communications may also occur when IMD 10 is alternatively configured as an external medical device or contains wired communication channels that extend from within the patient to points outside of the patient.

IMD 10 includes at least one sensor 22 configured to sense at least one physiological signal or condition, from which a physiological parameter can be determined. Sensors 22 can monitor electrical, mechanical, chemical, or optical information that contains physiological data of the patient and can utilize any source of physiological signals used for detecting ischemia, UA, AMI or any other physiological event or condition. In one or more embodiments, sensor 22 is configured to collect electrocardiogram (ECG) signals for use in deriving one or more heart rate related parameters, which can be used for ST segment analysis, heart rate analysis, Q-wave analysis, T-wave analysis, respiration analysis, activity analysis or other types of analyses that can utilize information contained in ECG signals. For example, sensor 22 may comprise a heart sensor, such as the MDT Reveal® system, commercially available from Medtronic of Minneapolis, that is capable of sensing cardiac activity, electrocardiograms, heart rate, or the like. Reveal is a registered trademark of Medtronic, Inc. of Minneapolis, Minn.

In one or more embodiments, sensor 22 is configured to measure thorax impedance for use in respiratory analysis, such as a change in respiratory rates, breathing depth, and/or minute ventilation. Impedance signals may be obtained from cardiac electrodes or auxiliary electrodes, for example in the manner used for determining minute ventilation in rate responsive pacemakers or may alternatively be provided as any physiological signal that varies in response to the respiration cycle. In one or more embodiments, sensor 22 includes an accelerometer for detecting physical activity and/or positioning of the patient.

Figure 3:
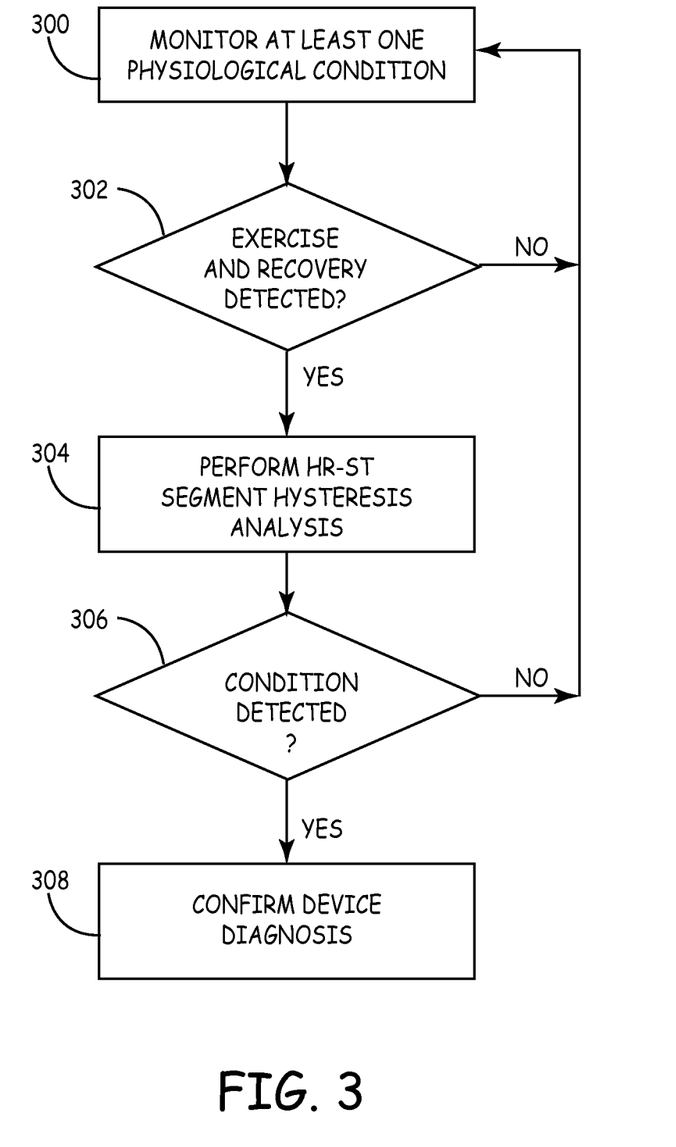
FIG. 3 is an operational flow diagram illustrating a process for detecting heart-related conditions in a device in accordance with one or more embodiments of the present disclosure.

Referring now to FIG. 3, an operation flow diagram is provided for one or more embodiments of detecting ischemia, UA, AMI or other heart-related conditions by obtaining information in real-time when a condition is initially identified as potentially occurring. The monitoring of physiological conditions for the detection of heart-related conditions according to the method of FIG. 3 may be performed continuously, or on a scheduled or triggered basis. For example, IMD 10 may be programmed to operate during certain hours or additionally or alternatively be enabled to be performed upon a triggering condition. A triggering condition may be an indicator based on an activity signal or other physiological signal or any combination thereof.

Condition monitoring begins by sensing at least one physiological signal or condition useful in detecting a heart-related condition at step 300. Each of these signals may be sensed simultaneously to allow multiple, concurrent physiological parameter values to be determined for use in detection procedures or may alternatively be performed sequentially and processed as required in stages. The physiological signals and corresponding parameters are initially monitored to detect a physical exercise and recovery episode by a patient during which the patient performs a certain level of physical exercise. In order to detect that the patient is physically exerting himself, a number of analyses of physiological parameters are performed. In one or more embodiments, an ECG signal is initially monitored to detect physical exercise activity by the patient by performing at least one of a heart rate analysis and a respiration analysis. In some embodiments, the exercise and recovery episode can further be detected by i) respiration analysis performed on thorax impedance signals or ii) physical activity analysis performed using accelerometer signals. In some embodiments, physiological parameters monitored may not be associated with actual physical exercise by the patient but may include non-physical exercise circumstances in which the heart rate, activity levels and other parameters of the patient are elevated in a similar manner as when the patient is exercising.

The method determines in step 302 whether an exercise and recovery episode is detected from the various analyses of physiological parameters that are performed. In one or more embodiments, the monitored physiological parameters (e.g., (heart rate, QT interval, respiratory parameters, patient activity levels, etc.) detect exercise by the patient in order to initiate the diagnostic procedures described herein, where it is understood that a recovery period will necessarily always follow an exercise period. Once the exercise and recovery episode is detected, a heart rate (HR)-ST segment deviation hysteresis analysis is performed by IMD 10 in step 304 from certain physiological parameters that are derived from physiological signals being monitored by IMD 10. The HR-ST segment deviation hysteresis analysis is performed on the detected exercise and recovery episode to detect ST segment depression or elevation to identify a probability that a certain heart-related condition is occurring. The HR-ST segment hysteresis analysis is also performed at the time when the exercise and recovery episode is detected in order to confirm that exercise or recovery occurred and also to provide real-time detection of a heart-related condition at the time when it is most likely to occur during exercise and recovery. In one or more embodiments, the monitored ECG signal provides HR information and ST segment information that is used in the HR-ST segment hysteresis analysis.

In one or more embodiments, the results of the HR-ST segment hysteresis analysis are utilized to detect in step 306 whether ischemia, UA, AMI or another heart-related condition are likely to be occurring in the patient. In one or more embodiments, other analyses can also be performed to assist in identifying whether a heart-related condition is likely to be occurring, such as but not limited to ST segment analysis, T-wave analysis (e.g., trend analysis and inversion), Q-wave analysis (e.g., duration and amplitude) or other physiological parameters.

In one or more embodiments, the HR-ST segment hysteresis analysis can be performed during successive exercise-recovery periods and compared against each other to identify trends in the measured/calculated parameters that may signify increasing levels of risk, thereby identifying an increased probability that an ischemia, UA, AMI or another heart-related event may be occurring in the patient. For example, changes in the HR-ST segment can signal increasing levels of risk and a heightened probability that a patient will suffer an AMI event. In one or more embodiments, the HR-ST segment hysteresis analysis can be performed during spontaneous events, where the intensity and duration of exercise can be assessed through the activity monitor and the associated ECG used to perform the HR-ST analysis.

In one or more embodiments, the HR-ST segment hysteresis analysis can be performed to assess HR-ST segment changes that are not necessarily associated with heightened levels of activity, such as to detect stress-related cardiac events. In one or more embodiments, the HR-ST segment hysteresis analysis can be performed during periods when the patient is experiencing certain symptoms to reveal whether such symptoms are due to non-cardiac related causes.

Once a desired level of probability that the heart-related condition has been detected by the analyses performed by IMD 10 is achieved, a device diagnosis or detection of the condition is generated. In one or more embodiments, the device diagnosis of the condition can be confirmed in step 308 through a variety of possible methodologies. In some embodiments, data utilized in the analyses can be transmitted remotely for clinical review and confirmation of the device's detection of the condition or the patient may be prompted to answer questions related to symptoms that patient is experiencing to confirm the probability that the condition is occurring in the patient.

Figure 6:
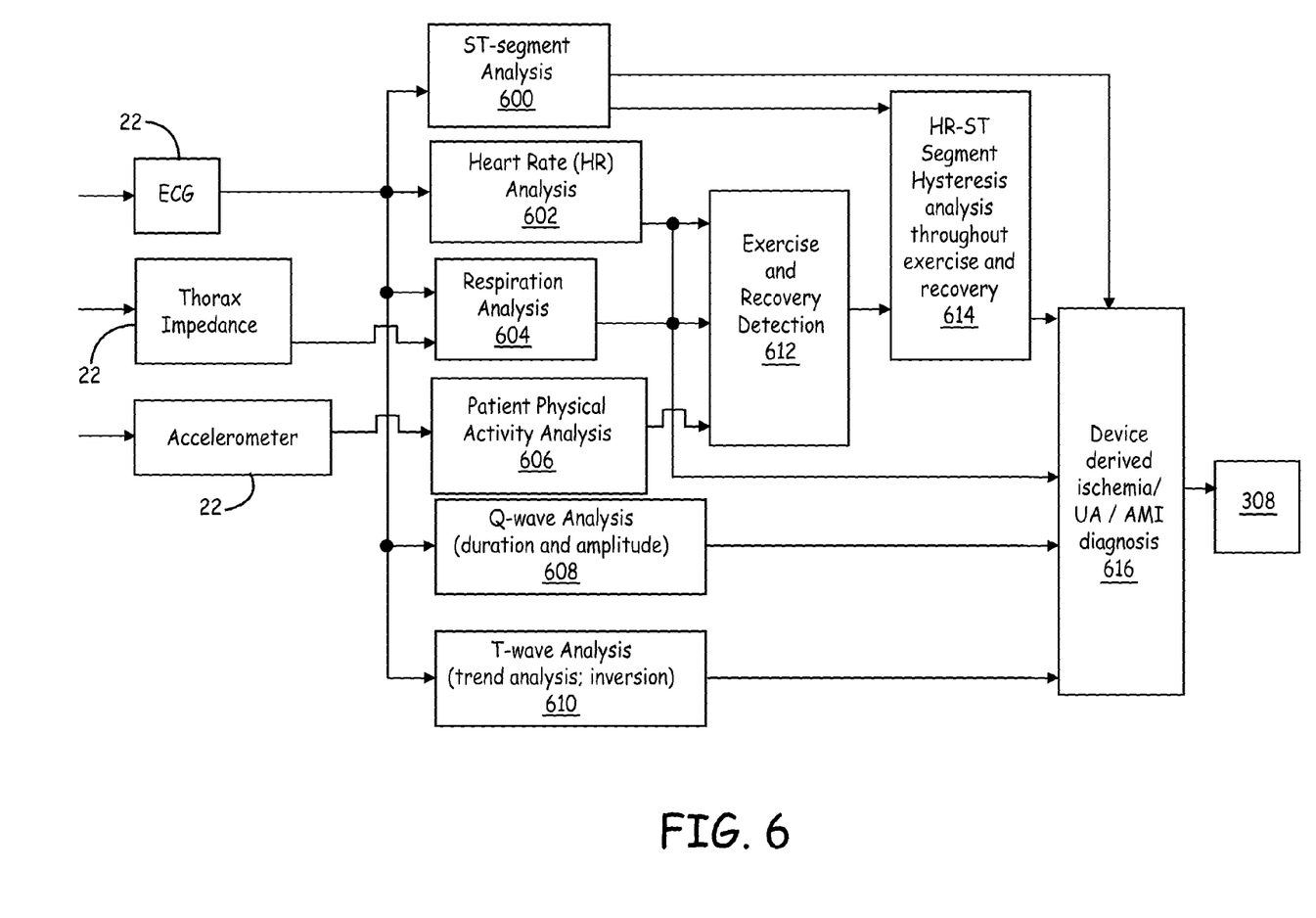
FIG. 6 is a block diagram illustrating various operational program modules implemented in an implantable medical device for detecting heart-related conditions in accordance with one or more embodiments of the present disclosure.

In one or more embodiments, the device's detection of the heart-related condition is performed by various routines or modules being executed by controller 24 from instructions stored in memory 26 to provide the functionality described herein. Referring not to FIG. 6, a block schematic illustration is provided in accordance with one or more embodiments of the various routines or modules executed by controller 24. A heart rate analysis module 602, respiration analysis module 604 and patient physical activity analysis module 606 receive physiological signals from various respective sensors 22 (e.g., ECG, thorax impedance, accelerometer) and derive respective physiological parameters there from. An exercise and recovery detection module 612 receives input of the physiological parameters from the heart rate analysis module 602, respiration analysis module 604 and patient physical activity analysis module 606 for use in detecting whether the patient is performing physical exercise to a desired level. Upon detection of an exercise and recovery period, a HR-ST segment hysteresis analysis module 614 performs analysis through the exercise and recovery period of HR-ST segment hysteresis. A device derived ischemia/UA/AMI diagnosis module 616 receives the results from the HR-ST segment hysteresis analysis module 614 as well as possibly ST segment analysis module 600, Q-wave analysis module 608 and T-wave analysis module 610 for determining with a desired level of probability that a particular heart-related condition has been detected by the analyses performed by IMD 10.

Figure 4:
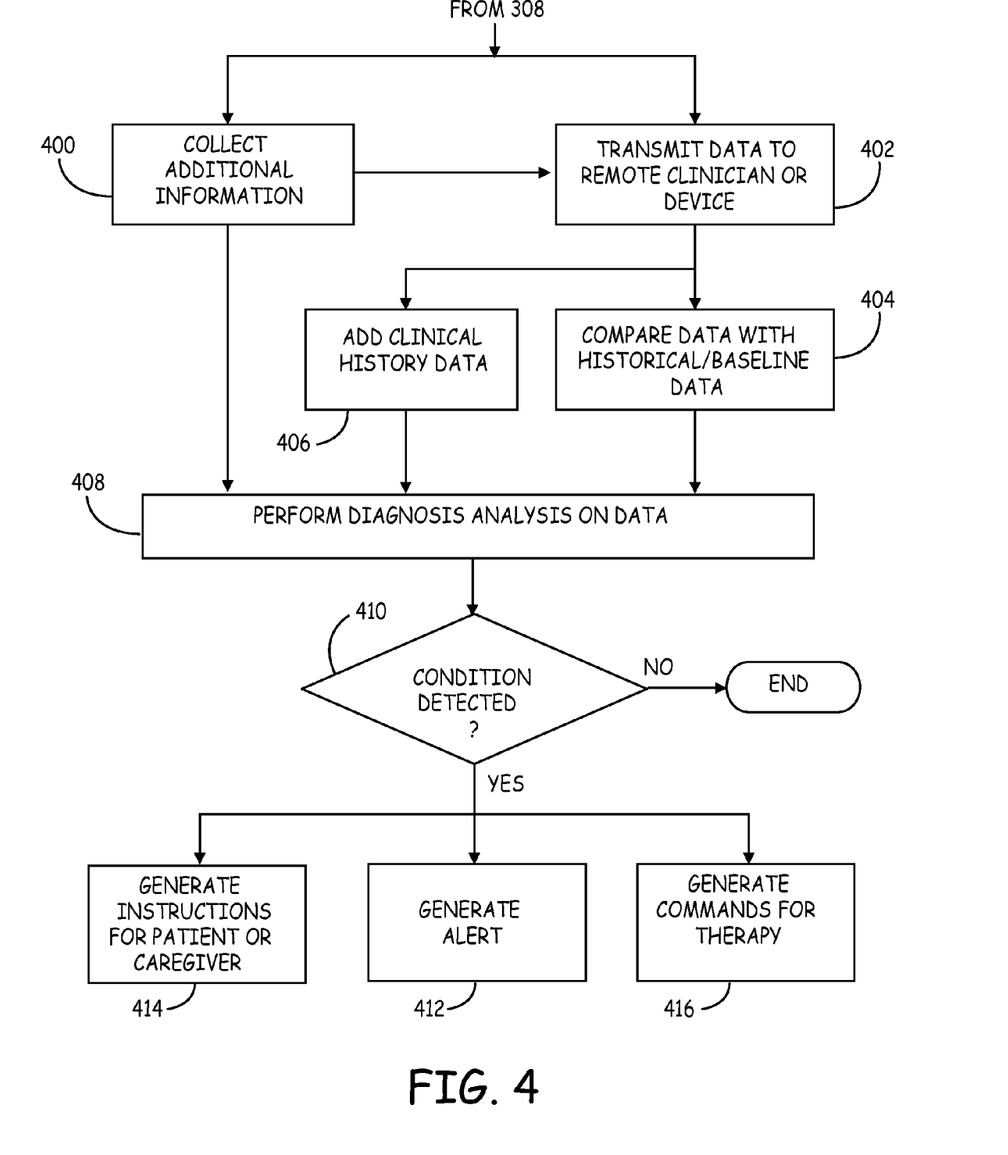
FIG. 4 is an operational flow diagram illustrating a process for confirming a device-detected heart-related condition in accordance with one or more embodiments of the present disclosure.

Referring now to FIG. 4, an operation flow diagram is provided for one or more embodiments of the method for confirming the probability of the device's diagnosis that the condition is occurring in the patient. In one or more embodiments, additional information may be collected at step 400 to confirm with greater certainty that the device's diagnosis that the condition is occurring in the patient is correct. In one or more embodiments, the additional collected information includes sensing additional physiological signals useful in detecting ischemia, UA, AMI or other heart-related conditions to determine whether these additional physiological signals also support a finding that conditions are occurring in the patient. In one or more embodiments, the additional collected information includes prompting a questionnaire to be presented to the patient or a caregiver in step 400 to provide responses to questions that may help determine whether the patient is experiencing certain symptoms associated with ischemia, AMI or other heart-related conditions (e.g., such as typical ischemic chest pain, the location of the pain or other symptoms). In one or more embodiments, additional collected information may be transmitted in step 402 to a physician, clinician or call center for use in further providing yet another added level of certainty of the detection of the heart-related disease by analyzing the symptoms being experienced by the patient. This allows a patient to provide symptoms the patient is experiencing during exercise immediately to a caregiver for analysis.

In one or more embodiments, the data utilized in the HR-ST segment hysteresis analysis by IMD 10 as well as data previously collected and stored by IMD 10 or other data related to other sensed physiological conditions can be transmitted in step 402 to a physician, clinician or call center for review either together, separately or in place with the responses to the symptom-related query. The actual data from the monitored physiological signals can then be compared against historical data for the patient or baseline data in step 404 to further to provide an added level of certainty to the detection of the heart-related condition. In some embodiments, clinical history data can further be added to the actual data in step 406 for use in the confirmation procedures.

Using the information and data collected from any of the above-described sources from steps 400, 402, 404 and 406, the data is analyzed in step 408 by the physician, clinician or call center representative or program to determine whether ischemia, UA, AMI or another heart-related condition is likely to be occurring in the patient. If it is determined at step 410 that the collection of information obtained from the various sources indicates with a certain probability that the patient is experiencing a heart-related condition, then a variety of possible alerts, reports, responses or actions can be performed.

In one or more embodiments, an alert can be generated in step 412 to notify the patient, a physician, an emergency response team, a hospital, the external device 30 or another individual or device that the patient has been diagnosed with a certain probability as experiencing the detected heart-related condition. In one or more embodiments, instructions can be generated in step 414 (e.g., transmitted through external device 30) to instruct the patient, emergency response personnel and/or bystanders to take appropriate actions to treat the detected condition, where such instructions could be part of a bi-directional communication that occurs with paramedics/physicians that were alerted of the detected condition. In one or more embodiments, instructions or commands may be provided to IMD 10 in step 416 (e.g., transmitted through external device 30 or another device) to activate different measurements, collect and send back additional data from measurements, or administer therapy to the patient.

Figure 5:
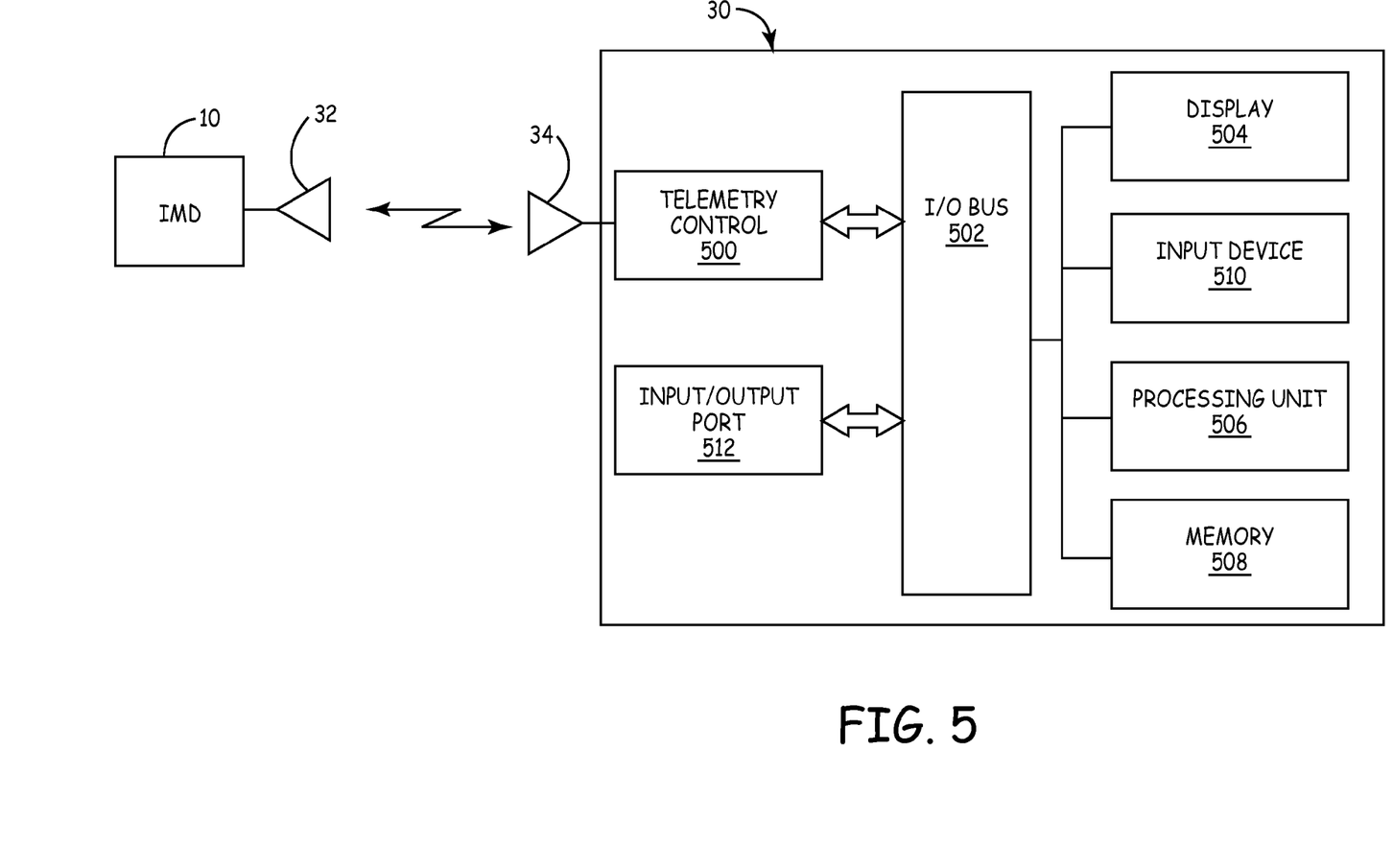
FIG. 5 is a block diagram illustrating the various components of one embodiment of an implantable medical device and external device configured to operate in accordance with one or more embodiments of the present disclosure.

In one or more embodiments, IMD 10 communicates with external device 30 in order to communicate data to the remote location (such as for accomplishing the procedures described in connection with FIG. 4) and in order to prompt the patient with the patient questionnaire. External device 30 includes processing circuitry for interpreting data received from IMD 10 and presenting the questionnaire to the patient on a display of external device 30 or another device. Referring now to FIG. 5, a block schematic illustration of external device 30 is provided in accordance with one or more embodiments. External device 30 includes an antenna 34, coil or wired input for communicating data and other signals between external device 30 and IMD 10. Data is received from IMD 10 through antenna 34, which is connected to telemetry/antenna control circuit or module 500 that serves to demodulate telemetry signals received through antenna 34. The demodulated signals are applied in parallel or serial digital format to input/output (I/O) unit or bus 502, where they in turn may be applied to a display or screen 504, provided to processing unit 506 and/or memory 508. Processing unit 506 includes any type of microprocessor, digital signal processor, application specific integrated circuit (ASIC), field programmable gate array (FPGA) or other integrated or discrete logic circuitry programmed or otherwise configured to control operating of the external device 30 and provide functionality as described herein. In one embodiment, processing unit 506 executes instructions stored in memory 508 to provide functionality as described herein.

In one or more embodiments, external device 30 includes an input device 510 that allows data, commands or selections to be input into the external device 30 by a patient, physician or clinician. Input device 510 may include, but is not limited to, at least one of the following: a keyboard, track ball, mouse, touch-sensitive displays, push buttons, magnetic readers, RF readers, tablets, styluses, microphones, voice recognizers, handwriting recognizers and any other device that allows a patient, physician or clinician to input data to external device. Processing unit 506 controls operation of display 504 and is responsive to commands received from input device 510. Memory 508 is suitable for storing data received from IMD 10, input device 510, processing unit 506 or other data or commands otherwise received by external device 30. External device may further include an input/output port 512 for connecting external device 30 to other devices, communication networks, phone lines, wireless devices, etc. When data received from IMD 10 through the telemetry uplink or the responses to the symptom-related query are to be transmitted to a remote location for further analysis, such information and data can be transmitted through input/output port 512 to a connected network or through telemetry control 500 to a wirelessly connected device. In one or more embodiments, external device 30 may relate information to the patient or a clinician by sound through speakers (not shown) in addition to or instead of presenting such information on display 504.

In one or more embodiments, external device 30 may be a portable device wearable or capable of being carried by the patient. In one or more embodiments, external device 30 may comprise an in-home monitoring device, such as the Medtronic CareLink® Network monitor, that collects information from IMDs implanted in patients and communicates such information to remote clinicians through the Internet, phone lines or wireless networks. Carelink is a registered trademark of Medtronic, Inc. of Minneapolis, Minn. In one or more embodiments, external device 30 may comprise a personal computer or mobile phone having a software program installed thereon configured for receiving data from IMD 10, processing such data and/or further communicating such data to a remote location or clinician for further analysis and/or processing.

When prompting the patient for additional information relating to more specific diagnosis of ischemia, AMI or another heart-related condition, the patient is provided at least one question on display 504 that the patient provides responses to through input device 510 or the patient is otherwise provided with the opportunity to input specific information relevant to the diagnosis of a particular condition. For example, the patient can describe specific symptoms (e.g., typical ischemic chest pain) and locations of symptoms that can used as a factor in the further diagnosing conditions with greater specificity. The information contained in the patient's responses can either be used directly by external device 30 in confirming the device's diagnosis of the condition or the information can be transmitted back to IMD 10 for further processing or to a remote location (e.g., the physician's office, hospital or another clinician) for further processing and analysis.

When a determination is made either in IMD 10 or at the remote location that the patient is experiencing a certain heart-related condition, in one or more embodiments it is determined whether the physiological parameters and/or responses to symptom-related queries and/or signal(s) meet a predefined threshold indicating a probability that the condition may be occurring. The predefined threshold may comprise a single threshold value related a single or combination of sensed physiological parameters, a plurality of threshold values with each respectively related to one of a plurality of physiological parameters, and/or weighted thresholds that are weighted for respective physiological parameters.

The method and apparatus for detecting ischemia, acute myocardial infarction or other heart-related conditions and providing a response thereto described in the various embodiments herein allow conditions to be diagnosed in near real-time to when they are initially experienced by a patient. This near-real time diagnosis is achievable by monitoring physical activity of the patient and utilizing markers having a superior discriminative capacity compared to convention markers. This allows diagnosis, responses and therapies to be delivered to the patient without significant delay, thereby adding to likelihood of the effectiveness of the therapy and treatment provided to the patient. Further, by implementing a detection procedures and analyses of HR-ST segment hysteresis data throughout a detected exercise and recovery period, an improved likelihood of detecting ischemia, acute myocardial infarction or other heart-related conditions is provided. Still further, by prompting a patient to enter a number of symptom-related questions immediately upon physiological signals providing an indication of a condition, typical ischemic chest pain can be diagnosed and used in detecting heart-related conditions at an early stage before a patient may typically bring such pains to the attention of a physician. Conventionally, it has been difficult for a patient to associate such symptoms with the occurrence of a heart-related condition, whereas the present system and method allow the patient's symptoms to immediately be diagnosed through the triggering of sensed physiological parameters.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
 detecting an exercise and recovery episode in a patient using an implantable medical device (IMD);
 performing an analysis of heart rate (HR)-ST segment hysteresis over the exercise and recovery episode using the IMD; and
 determining whether the patient is experiencing a particular heart-related condition based on the results of the HR-ST segment hysteresis analysis.

2. The method of claim 1, wherein the heart-related condition includes at least one of an ischemia, unstable angina and an acute myocardial infarction, the method further comprising determining whether the patient is experiencing a particular heart-related condition by computing a probability that the particular heart-related condition is occurring and determining whether the computed probability exceeds a predefined detection threshold.

3. The method of claim 1, wherein the HR-ST segment hysteresis analysis includes at least one of (i) a detailed analysis of an initial recovery period after exercise ceases, (ii) a determination of a prevailing direction of HR-ST hysteresis during the exercise and recovery episode, and (iii) a determination of an average magnitude of HR-ST hysteresis during the exercise and recovery episode.

4. The method of claim 1, further comprising collecting additional information from a patient relating to symptoms being experienced by the patient for use in confirming the detection of the particular heart-related condition.

5. The method of claim 4, wherein the additional information is collected by querying the patient with symptom-related questions after a certain level of probability that the patient is experiencing a particular heart-related condition is reached from the HR-ST segment hysteresis analysis.

6. The method of claim 1, wherein upon a determination that the patient is experiencing a particular heart-related condition based on the results of the HR-ST segment hysteresis analysis, the method further comprising comparing data used in making such determination against at least one of historical data for the patient and baseline data for confirming the detection of the particular heart-related condition.

7. The method of claim 1, further comprising detecting the exercise and recovery episode by sensing at least one physiological signal and deriving a corresponding physiological parameter from each sensed signal.

8. The method of claim 7, wherein the physiological signals comprise at least one of a cardiac electrical signal and a respiratory signal.

9. The method of claim 7, wherein the at least one physiological signal comprises a patient activity signal generated by a sensor.

10. The method of claim 9, wherein the sensor comprises an accelerometer.

11. The method of claim 1, further comprising sensing an electrocardiogram (ECG) signal for deriving Q-wave and T-wave information from the ECG signal for use in confirming the detection of the particular heart-related condition.

12. The method of claim 1, further comprising generating an alert signal using the IMD upon the determination that the patient is experiencing a particular heart-related condition, the alert signal providing at least one of a notification of the detection of the heart-related condition and an instruction for treating the heart-related condition.

13. A system comprising:
 at least one physiological sensor configured to sense a corresponding physiological signal in a patient;
 a controller configured to derive a corresponding physiological parameter from each sensed signal and to detect an exercise and recovery episode in the patient; and
 a housing configured for implantation in the patient, wherein the at least one physiological sensor and the controller are included in the housing, and
 wherein the controller is further configured to:

collect ST-segment information from a corresponding physiological sensor;

perform an analysis of heart rate (HR)-ST segment hysteresis over the exercise and recovery episode; and determine whether the patient is experiencing a particular heart-related condition based on the results of the HR-ST segment hysteresis analysis.

14. The system of claim 13, wherein the controller is further configured to generate a command to an external device to query the patient with symptom-related questions after a certain level of probability that the patient is experiencing a particular heart-related condition is reached from the HR-ST segment hysteresis analysis.

15. The system of claim 13, wherein the at least one physiological sensor is configured to sense at least one of a cardiac electrical signal and a respiratory signal.

16. The system of claim 13, wherein the controller is further configured to communicate sensed physiological sensor data to a remote device for use in comparing the sensed data against at least one of historical data for the patient and baseline data for confirming the detection of the particular heart-related condition.

17. The system of claim 13, wherein the at least one physiological sensor is configured to sense a patient activity signal.

18. The system of claim 17, wherein the at least one physiological sensor includes an accelerometer.

19. A system comprising:
means for detecting an exercise and recovery episode in a patient using an implantable medical device (IMD);
means for performing an analysis of heart rate (HR)-ST segment hysteresis over the exercise and recovery episode using the IMD; and
means for determining whether the patient is experiencing a particular heart-related condition based on the results of the HR-ST segment hysteresis analysis.

20. The system of claim 19, further comprising means for performing the HR-ST segment hysteresis analysis by performing at least one of (i) a detailed analysis of an initial recovery period after exercise ceases, (ii) a determination of a prevailing direction of HR-ST hysteresis during the exercise and recovery episode, and (iii) a determination of an average magnitude of HR-ST hysteresis during the exercise and recovery episode.

21. The system of claim 19, further comprising means for initiating a query containing questions relating to symptoms being experienced by the patient for use in confirming the detection of the particular heart-related condition.

22. The system of claim 19, further comprising:
means for deriving data related to at least one physiological parameter corresponding to a sensed physiological signal; and
means for communicating the physiological parameter data to a remote location for use in comparing the sensed data against at least one of historical data for the patient and baseline data for confirming the detection of the particular heart-related condition.

23. The system of claim 19, further comprising means for generating an alert signal using the IMD upon the determination that the patient is experiencing a particular heart-related condition, the alert signal providing at least one of a notification of the detection of the heart-related condition and an instruction for treating the heart-related condition.

24. The system of claim 19, further comprising means for detecting the exercise and recovery episode by sensing at least one physiological signal and deriving a corresponding physiological parameter from each sensed signal, wherein the at least one physiological signal comprises a patient activity signal generated by a sensor of the IMD.

25. The system of claim 24, wherein the sensor of the IMD comprises an accelerometer.

* * * * *